(12) United States Patent
Hagiwara

(10) Patent No.: US 12,419,608 B2
(45) Date of Patent: Sep. 23, 2025

(54) ELECTRONIC ENDOSCOPE SYSTEM FOR ATTENUATING NOISE IN ULTRASOUND IMAGES USING FILTER PROCESSING AND PULSE DURATION ADJUSTMENT

(71) Applicant: HOYA CORPORATION, Tokyo (JP)

(72) Inventor: Masayuki Hagiwara, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

(21) Appl. No.: 18/293,092

(22) PCT Filed: Sep. 21, 2022

(86) PCT No.: PCT/JP2022/035202
§ 371 (c)(1),
(2) Date: Jan. 29, 2024

(87) PCT Pub. No.: WO2023/063040
PCT Pub. Date: Apr. 20, 2023

(65) Prior Publication Data
US 2024/0324987 A1  Oct. 3, 2024

(30) Foreign Application Priority Data

Oct. 14, 2021  (JP) .................................. 2021-169093

(51) Int. Cl.
*A61B 8/00* (2006.01)
*A61B 8/12* (2006.01)
*A61B 8/14* (2006.01)

(52) U.S. Cl.
CPC .................. *A61B 8/12* (2013.01); *A61B 8/14* (2013.01); *A61B 8/4444* (2013.01); *A61B 8/5207* (2013.01); *A61B 8/5269* (2013.01)

(58) Field of Classification Search
CPC ........... A61B 8/12; A61B 8/14; A61B 8/4444; A61B 8/5207; A61B 8/5269
See application file for complete search history.

(56) References Cited

U.S. PATENT DOCUMENTS

2004/0030367 A1*  2/2004  Yamaki ................ A61B 1/0005
                                                                607/60
2007/0164632 A1*  7/2007  Adachi .............. G01N 29/2437
                                                                310/311
(Continued)

FOREIGN PATENT DOCUMENTS

EP        3628235 A1 *  4/2020  ........... A61B 8/0841
JP      2009-136626 A      6/2009
(Continued)

OTHER PUBLICATIONS

International Search Report issued in WIPO Patent Application No. PCT/JP2022/035202, dated Dec. 13, 2022, along with an English translation thereof.

(Continued)

*Primary Examiner* — Joel Lamprecht
*Assistant Examiner* — James F McDonald, III
(74) *Attorney, Agent, or Firm* — GREENBLUM & BERNSTEIN, P.L.C.

(57) ABSTRACT

An electronic endoscope system that acquires an ultrasonic image, and the electronic endoscope system includes: an electronic endoscope including, an image sensor that captures an image of a biological tissue, and an ultrasonic probe that applies ultrasonic waves to the biological tissue to obtain an echo signal; a captured image processor including an image processing unit that processes an imaging signal output from the image sensor and generates a captured image; and an ultrasonic image processor including an ultrasonic image processing unit that processes the echo signal output from the ultrasonic probe and generates an ultrasonic image, a frequency band detection unit that detects a frequency band of a noise component included in the echo signal and equal to or higher than a preset threshold level, and a filter processing unit that performs filter pro- (Continued)

cessing on the echo signal such that a signal in the detected frequency band is attenuated.

6 Claims, 13 Drawing Sheets

(56) References Cited

U.S. PATENT DOCUMENTS

| | | | | |
|---|---|---|---|---|
| 2008/0139946 | A1* | 6/2008 | Adachi | B06B 1/0292 600/463 |
| 2010/0036255 | A1 | 2/2010 | Itani | |
| 2011/0313320 | A1* | 12/2011 | Gewolb | A61B 5/4211 600/586 |
| 2016/0157828 | A1* | 6/2016 | Sumi | G01N 29/46 702/189 |
| 2017/0014099 | A1* | 1/2017 | Morimoto | A61B 8/461 |
| 2018/0253830 | A1 | 9/2018 | Courtney et al. | |
| 2019/0129026 | A1* | 5/2019 | Sumi | G01S 7/52041 |
| 2019/0365350 | A1 | 12/2019 | Chiang | |
| 2020/0000429 | A1* | 1/2020 | Morimoto | A61B 8/445 |
| 2023/0097283 | A1 | 3/2023 | Hagiwara | |

FOREIGN PATENT DOCUMENTS

| | | | |
|---|---|---|---|
| JP | 2010-42048 A | | 2/2010 |
| JP | 2014-3801 A | | 1/2014 |
| JP | 2018094235 A | * | 6/2018 |
| JP | 2019-534110 A | | 11/2019 |
| JP | 2020-508168 A | | 3/2020 |
| JP | 2021-137355 A | | 9/2021 |

OTHER PUBLICATIONS

Written Opinion issued in WIPO Patent Application No. PCT/JP2022/035202, dated Dec. 13, 2022.

Notice of Reasons for Refusal issued in related Japanese Patent application No. 2021-169093, dated Aug. 6, 2024, together with an English translation.

* cited by examiner

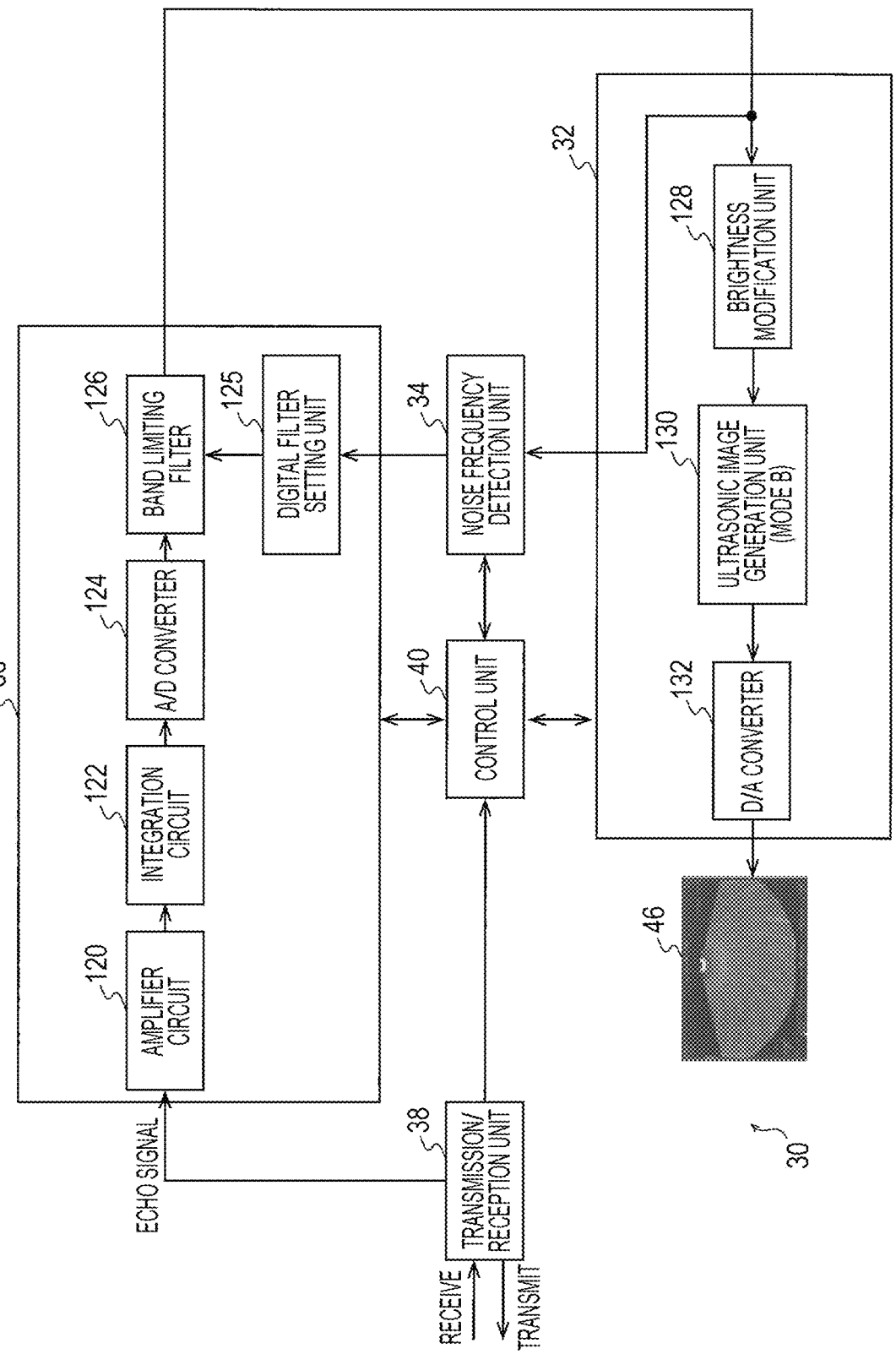

FIG. 5A
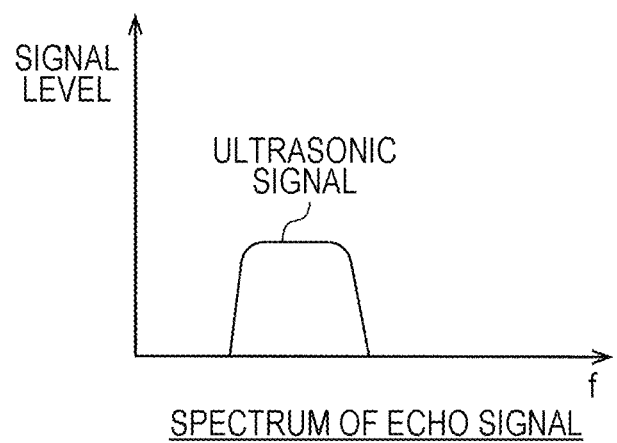
SPECTRUM OF ECHO SIGNAL
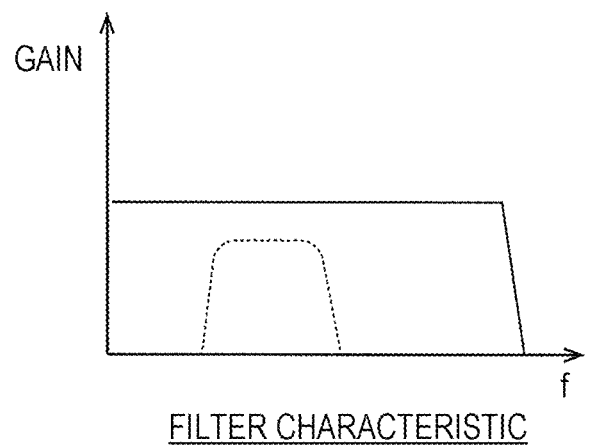
FILTER CHARACTERISTIC

FIG. 5B
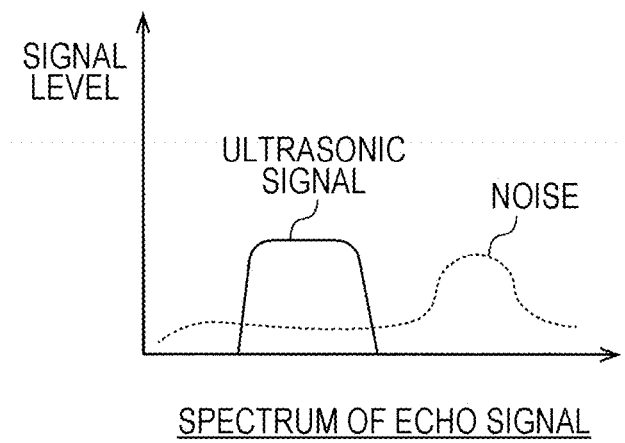
SPECTRUM OF ECHO SIGNAL
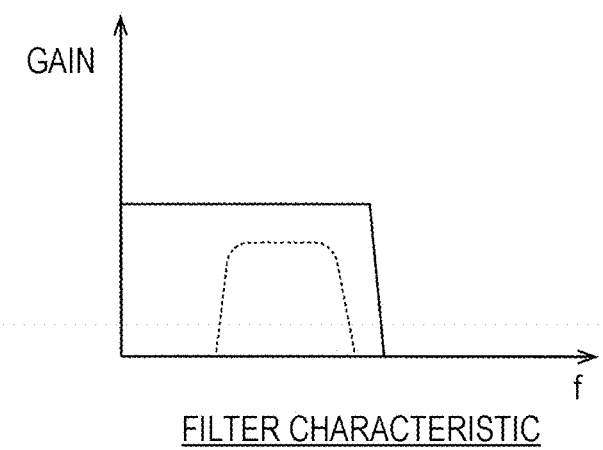
FILTER CHARACTERISTIC

FIG. 5C
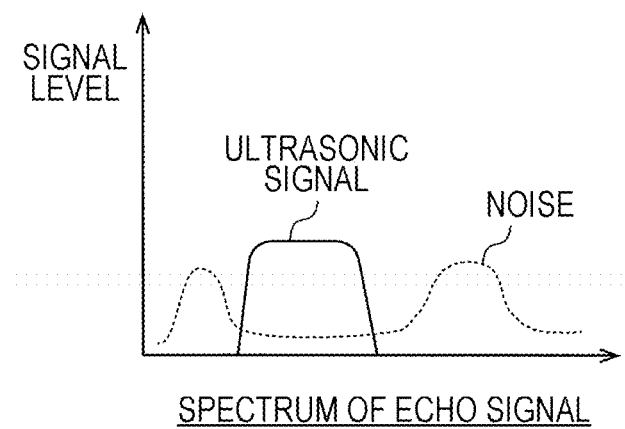
SPECTRUM OF ECHO SIGNAL
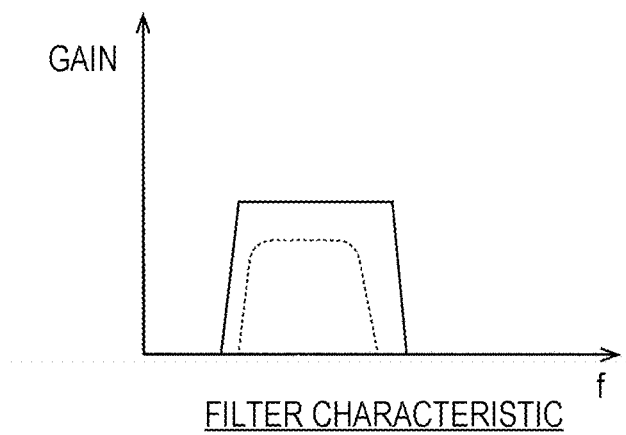
FILTER CHARACTERISTIC

FIG. 7
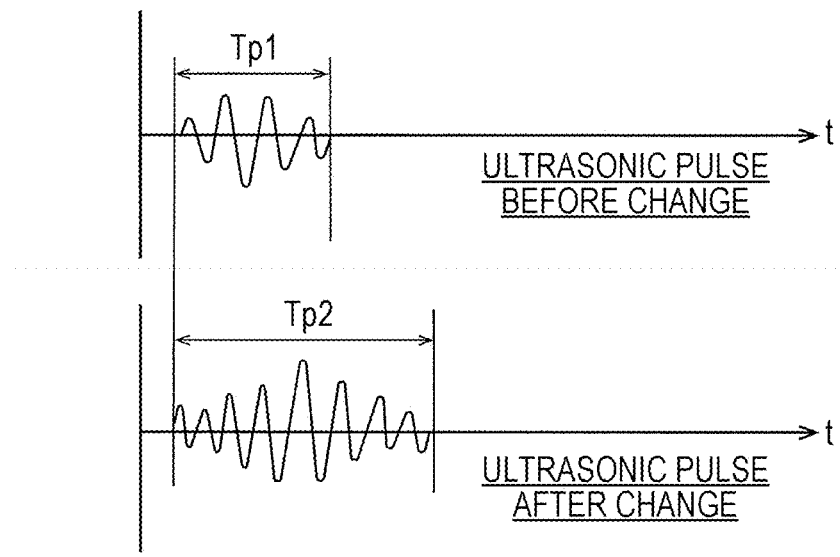
ULTRASONIC PULSE BEFORE CHANGE
ULTRASONIC PULSE AFTER CHANGE
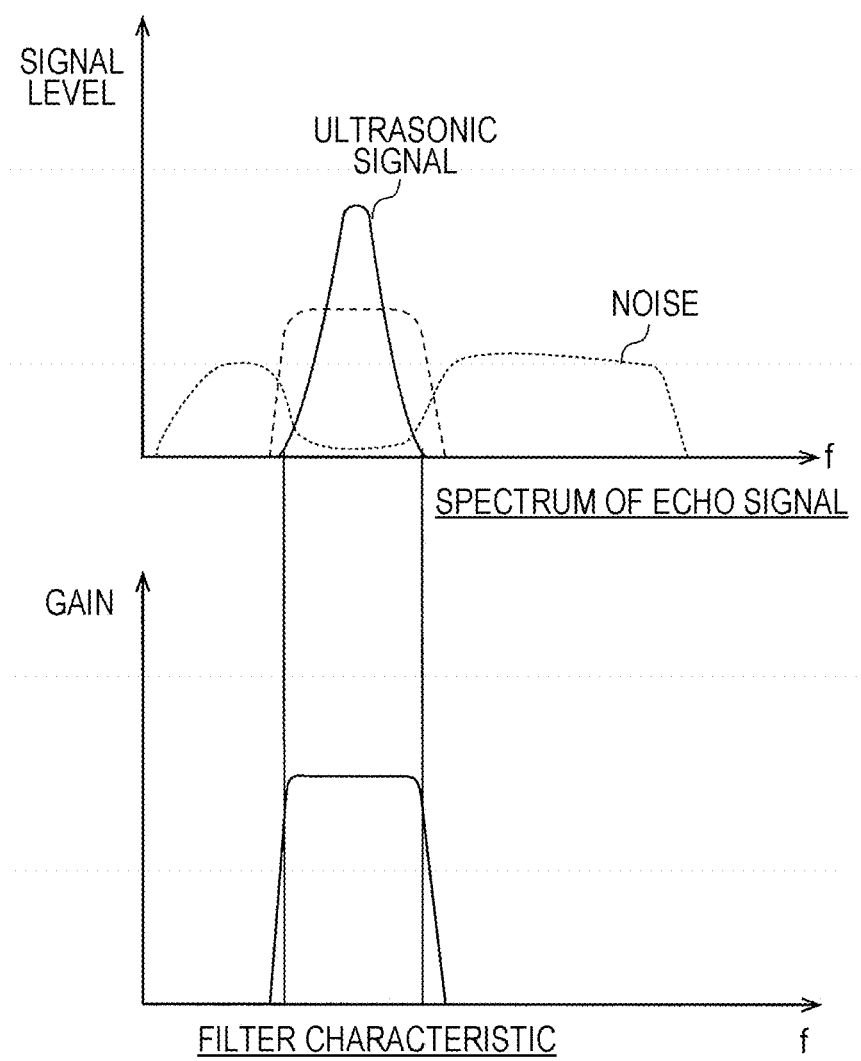
SPECTRUM OF ECHO SIGNAL
FILTER CHARACTERISTIC

ELECTRONIC ENDOSCOPE SYSTEM FOR ATTENUATING NOISE IN ULTRASOUND IMAGES USING FILTER PROCESSING AND PULSE DURATION ADJUSTMENT

TECHNICAL FIELD

The present invention relates to an electronic endoscope system that acquires an ultrasonic image.

BACKGROUND ART

An electronic endoscope system is used for observation and treatment of a biological tissue inside a human body. In addition to acquiring an optical observation image of a subject by using an image sensor as an image of a biological tissue, the electronic endoscope system is capable of obtaining an ultrasonic image (ultrasonic tomographic image) by using an endoscopic ultrasonography which includes an ultrasonic probe. A processor connected to the endoscopic ultrasonography functions as an ultrasonic diagnostic device and performs examination and diagnosis. Hereinafter, an endoscope that includes an image sensor and an ultrasonic probe is referred to as an endoscopic ultrasonography (or an electronic endoscope).

An endoscopic ultrasonography includes an image sensor and an ultrasonic probe. In a flexible tube extending from the endoscopic ultrasonography to a processor, an imaging signal transmission line is installed that connects the image sensor provided at a distal tip of an insertion portion to a connector connected to the processor. An imaging signal is transmitted through the imaging signal transmission line. Further, in the above flexible tube, an ultrasonic signal transmission line is installed that connects the ultrasonic probe provided at the distal tip of the insertion portion to the connector connected to the processor. An ultrasonic signal is transmitted through the ultrasonic signal line.

When examination or diagnosis is performed using ultrasonic waves, power is supplied from the processor to the ultrasonic probe, and the ultrasonic probe transmits ultrasonic waves to a biological tissue and receives reflected waves. The reflected waves received by the ultrasonic probe are converted into an echo signal, and the echo signal is sent to the processor through the ultrasonic signal transmission line and subjected to signal processing performed by the processor to obtain an ultrasonic image.

The processor includes a switching power supply in addition to a signal processing unit that performs data processing by using a transmission signal (ultrasonic signal, imaging signal) from the endoscopic ultrasonography, a control unit that controls an image display, and the like. The switching power supply generates and supplies a necessary voltage for operating each constituent device in the endoscopic ultrasonography and the processor. The processor is connected to a monitor for displaying captured images and ultrasonic images.

In an ultrasonic image, which is obtained based on the echo signal of the ultrasonic probe and displayed on the monitor, noise generated in the endoscopic ultrasonography or in the processor, or noise superimposed on an AC power supply and entering from outside is sometimes mixed as a noise component. The noise component includes, for example, a noise component caused by switching of the switching power supply or a noise component caused by mutual interference between the above transmission lines. For example, in the flexible tube, because the imaging signal transmission line and the ultrasonic signal transmission line are provided close to each other, electrostatic coupling or electromagnetic coupling between the transmission lines becomes strong, and a pulse control signal or the like for controlling the image sensor interferes with the ultrasonic probe or the ultrasonic signal transmission line, thereby causing a noise component to be mixed with the echo signal.

Furthermore, in the ultrasonic image, ultrasonic-specific noise called artifacts (virtual images that do not actually exist) is sometimes also generated. An echo signal is obtained due to an ultrasonic wave being generated and an echo reflected from the inside of a living body being received. However, a virtual image, that is, an artifact is generated as noise due to factors such as side lobe artifacts, grating lobes, and multiple reflection. Further, when high-frequency noise generated by the switching power supply is superimposed on a reception signal of the ultrasonic signal, an artifact sometimes appears in the ultrasonic image generated in an ultrasonic diagnostic image.

JP 2014-003801 A discloses an ultrasonic image processor that is capable of removing periodic noise caused by an operation of a DC/DC converter from the noise components in the ultrasonic image. A main converter that inputs power from a power input unit and outputs power of a constant voltage, and a plurality of sub-converters that inputs power of the constant voltage and outputs power to a circuit constituting the ultrasonic image processor are included, and switching operations of the main converter and the sub-converters are synchronized to reduce spike noise.

SUMMARY OF INVENTION

Technical Problem

However, in the above-described conventional ultrasonic image processor, although periodic noise can be removed, unintended noise cannot be reduced.

For example, unintended noise superimposed on an AC power supply may intrude into an ultrasonic diagnostic device. Further, in a case where a plurality of devices operates, unintended noise may intrude into the ultrasonic diagnostic device. For example, in a case where an endoscope and the ultrasonic diagnostic device operate simultaneously as in an endoscopic ultrasonography system, an electromagnetic wave accompanying an operation of the endoscope is guided by an ultrasonic probe, and noise is generated.

In a case where unintended noise is mixed in an ultrasonic system in this way, there is a problem that the noise cannot be effectively removed.

Thus, an object of the present invention is to provide an electronic endoscope system that is capable of, when an ultrasonic image is acquired using an ultrasonic probe, suppressing a noise component included in the ultrasonic image, and generating a high-quality ultrasonic image.

Solution to Problem

An aspect of the present invention is an electronic endoscope system that acquires an ultrasonic image, and the electronic endoscope system includes:
an electronic endoscope including, at a distal tip, an image sensor that captures an image of a biological tissue, and an ultrasonic probe that applies ultrasonic waves to the biological tissue to obtain an echo signal;
a captured image processor including an image processing unit that processes an imaging signal output from the image sensor and generates a captured image; and an ultrasonic image processor including an ultrasonic image processing unit that processes the echo signal output from the ultrasonic probe and generates an ultrasonic image, a frequency band detection unit that detects a frequency band of a noise component included in the echo signal and equal to or higher than a preset threshold level, and a filter processing unit that performs filter processing on the echo signal such that a signal in the detected frequency band is attenuated.

The ultrasonic image processor may include a low-pass filter that attenuates a signal of a frequency component equal to or higher than a predetermined frequency in the echo signal, and the filter processing unit may perform the filter processing such that a signal of a frequency component equal to or higher than a frequency lower than the predetermined frequency in the echo signal is attenuated.

The echo signal may include a signal component of a fundamental frequency and equal to or greater than two harmonic components having a frequency N times the fundamental frequency (N: an integer of equal to or greater than 2), the ultrasonic image processing unit may generate the ultrasonic image on the basis of the equal to or greater than two harmonic components, and the filter processing unit may perform the filter processing on the echo signal such that a signal having a frequency other than the frequency N times the fundamental frequency is attenuated.

The ultrasonic image processor may include an adjustment unit that adjusts pulse duration of an ultrasonic wave applied to the biological tissue by the ultrasonic probe, and the filter processing unit may perform filter setting on the filter processing on the basis of the pulse duration adjusted by the adjustment unit.

The ultrasonic image processor may include a frequency changing unit that changes a frequency of an ultrasonic wave applied to the biological tissue by the ultrasonic probe in such a way as not to overlap with the frequency band of the noise component detected by the frequency band detection unit.

The ultrasonic image processing unit may perform gain change processing in such a way as to change an amplification gain value between a noise pixel and a pixel other than the noise pixel in the ultrasonic image corresponding to the noise component.

The ultrasonic image processing unit may replace a pixel value at a noise pixel position in the ultrasonic image corresponding to the noise component with an interpolation pixel value generated on the basis of pixel values of peripheral pixels positioned around the noise pixel position.

Advantageous Effects of Invention

According to the above-described electronic endoscope system, it is possible to, when an ultrasonic image is acquired using an ultrasonic probe, suppress a noise component included in the ultrasonic image, and generate a high-quality ultrasonic image.

BRIEF DESCRIPTION OF DRAWINGS

FIG. 4 is a diagram for describing an example of signal processing until an echo signal when an ultrasonic image is acquired is displayed as a mode-B ultrasonic image in the electronic endoscope system of the embodiment.

FIG. 5A is a diagram for describing an example of a filter characteristic applied to an echo signal.

FIG. 5B is a diagram for describing an example of the filter characteristic applied to the echo signal.

FIG. 5C is a diagram for describing an example of the filter characteristic applied to the echo signal.

FIG. 7 is a diagram for describing an example of the filter characteristic applied to the echo signal.

DESCRIPTION OF EMBODIMENTS

An electronic endoscope system of an embodiment includes a captured image processor and an ultrasonic image processor.

The captured image processor includes an electronic endoscope including, at a distal tip, an image sensor that captures an image of a biological tissue and an ultrasonic probe that applies ultrasonic waves to the biological tissue to obtain an echo signal, and an image processing unit that generates a captured image by processing an imaging signal output from the image sensor. The ultrasonic image processor includes an ultrasonic image processing unit, and processes an echo signal output from the ultrasonic probe to generate an ultrasonic image.

Here, the echo signal output from the ultrasonic probe may include unintended noise superimposed on an AC power supply that operates the electronic endoscope system. Further, in the echo signal, an electromagnetic wave accompanying an operation of the electronic endoscope is guided by the ultrasonic probe, and noise may be generated. Such unintended noise sometimes appears in the generated ultrasonic image and degrade accuracy of the image.

Thus, in the electronic endoscope system of the embodiment, the ultrasonic image processor includes a frequency band detection unit and a filter processing unit in order to effectively suppress unintended noise.

The frequency detection unit detects a frequency band of a noise component included in an echo signal and equal to or higher than a preset threshold level. The filter processing unit performs filter processing on an echo signal so that a signal in a frequency band detected by the frequency band detection unit is attenuated. That is, since the filter processing unit performs the filter processing on the echo signal in consideration of a frequency band of a detected noise component, it is possible to effectively suppress unintended noise.

Note that, in the following description, a signal that does not include noise in an echo signal is referred to as an "ultrasonic signal". That is, in the present disclosure, the ultrasonic signal is a signal included in a reflected wave (echo signal) from a subject due to only an ultrasonic wave transmitted according to a drive signal. Actually, the echo signal is obtained by adding noise to the ultrasonic signal.

(Overall Configuration of Electronic Endoscope System)

Figure 1:
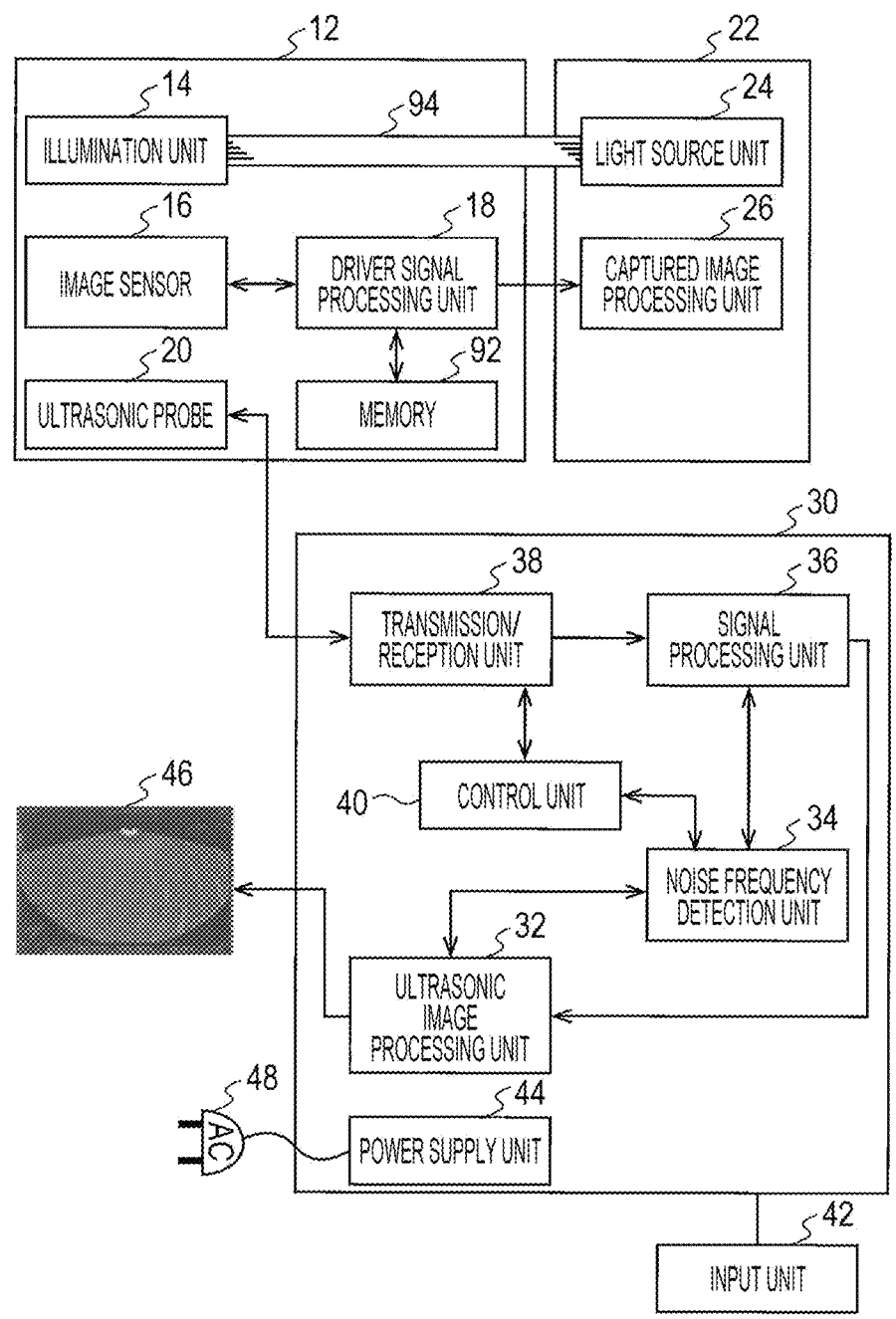
FIG. 1 is a block diagram illustrating an example of an overall configuration of an electronic endoscope system of an embodiment.

FIG. 1 is a block diagram illustrating an overall configuration of the electronic endoscope system of the embodiment. An electronic endoscope system 10 that acquires an ultrasonic image includes an electronic endoscope 12, a captured image processor 22, and an ultrasonic image processor 30.

(Electronic Endoscope 12)

The electronic endoscope 12 includes an illumination unit 14 that irradiates a biological tissue, an image sensor 16 that captures an image of the biological tissue, a driver signal processing unit 18 that preprocesses a signal captured by the image sensor 16, an ultrasonic probe 20 that applies ultrasonic waves to the biological tissue to obtain an echo signal, and a memory 92. The ultrasonic probe 20 is a phased array-type probe that is capable of acquiring echo signals along various directions by a plurality of probe elements which is arranged in a predetermined direction and each of which outputs ultrasonic waves at predetermined time intervals.

An image signal of the biological tissue is input from the image sensor 16 to the driver signal processing unit 18 in predetermined frame periods, and is output to a captured image processing unit 26 of the captured image processor 22. The frame period is, for example, 1/30 seconds or 1/60 seconds.

The driver signal processing unit 18 also accesses the memory 92 and reads specific information of the electronic endoscope 12. The specific information of the electronic endoscope 12 recorded in the memory 92 includes, for example, the number of pixels or sensitivity of the image sensor 16, an operable frame rate, a model number, and the like.

(Captured Image Processor 22)

The captured image processor 22 includes a light source unit 24 that transmits a light source to the illumination unit 14, and the captured image processing unit 26 that generates a captured image by processing an imaging signal output from the image sensor 16.

The light source unit 24 transmits illumination light to the illumination unit 14 of the electronic endoscope 12 through a light guide 94. As the light source, for example, a high brightness lamp such as a xenon lamp, a halogen lamp, a mercury lamp, or a metal halide lamp is used. The illumination light transmitted from the light source is condensed by a condenser lens (not illustrated), and is limited to an appropriate light amount via an aperture. A motor is mechanically connected to the aperture via a transmission mechanism such as an arm or a gear (not illustrated). An opening degree of the aperture can be changed in order to make brightness of a video displayed on a display screen of a captured image display unit (not illustrated) appropriate.

As the light source of the light source unit 24, instead of a white light source that emits white light, a semiconductor light emitting element such as a light emitting diode or a laser diode that emits light in a predetermined wavelength region may be used.

The captured image processing unit 26 is provided with a pre-stage signal processing circuit, and performs demosaic processing on each of R, G, and B image signals input from the driver signal processing unit 18 in a frame period. Specifically, interpolation processing using peripheral pixels G and B is performed on each R image signal, interpolation processing using peripheral pixels R and B is performed on each G image signal, and interpolation processing using peripheral pixels R and G is performed on each B image signal. As a result, all the image signals are converted into image data having information of the three color components R, G, and B. Furthermore, the pre-stage signal processing circuit performs well-known processing such as color correction, matrix calculation, and white balance correction.

The captured image processing unit 26 may include a post-stage signal processing circuit. The post-stage signal processing circuit performs predetermined signal processing on image data to generate moving image data, and converts the moving image data into a predetermined video format signal. The video format signal obtained by the conversion is used for displaying a moving image on a display unit 46. As a result, a moving image of the biological tissue is displayed on the display screen.

(Ultrasonic Image Processor 30)

The ultrasonic image processor 30 includes a transmission/reception unit 38, an ultrasonic image processing unit 32, a noise frequency detection unit 34, a signal processing unit 36, and a control unit 40.

The transmission/reception unit 38 transmits a drive signal to the ultrasonic probe 20, and receives an echo wave (echo signal). The signal processing unit 36 performs predetermined signal processing including binarization processing on an echo signal received by the transmission/reception unit 38. The ultrasonic image processing unit 32 generates an ultrasonic image on the basis of an echo signal processed by the signal processing unit 36.

The noise frequency detection unit 34 detects a frequency of noise included in an echo signal subjected to predetermined signal processing performed by the signal processing unit 36. Detailed configurations of the noise frequency detection unit 34 and the signal processing unit 36 will be described later.

The control unit 40 mainly includes a microprocessor, and controls each unit in the ultrasonic image processor 30.

On the basis of a digital echo signal, the ultrasonic image processing unit 32 performs predetermined calculation as grayscale image data by, for example, brightness modification, and generates a one-dimensional mode-B image along one direction. Furthermore, the ultrasonic image processing unit 32 creates one two-dimensional mode-B image by arranging, along a predetermined azimuth direction in accordance with phased array scanning, one-dimensional mode-B images along a plurality of directions generated on the basis of an echo signal obtained from the phased array-type ultrasonic probe 20. Furthermore, on the created image, image processing using known technologies such as gain processing and contrast processing is performed and shade processing corresponding to an image display range of the display unit 46 is performed.

The ultrasonic image processor 30 includes the display unit 46 that has a display for a generated ultrasonic image and an input function that enables inputs using a touch-panel system. Furthermore, the ultrasonic image processor 30 includes an input unit 42 that operates the ultrasonic image processor 30, a power supply unit 44, and an AC power input unit 48.

The input unit 42 receives inputs of various types of information by using a keyboard, a mouse, a touch panel, or the like. The display unit 46 displays various types of information including a generated ultrasonic image.

The power supply unit 44 supplies, on the basis of an AC power supply input from the AC power input unit 48, power for driving the electronic endoscope 12 and the captured image processor 22 in addition to the ultrasonic image processor 30. The power supply unit 44 includes, as a constituent device, a DC/DC converter as a switching power supply, for example, and generates a DC voltage using a switching frequency of the DC/DC converter. A plurality of DC/DC converters is provided, and each DC/DC converter converts an input DC voltage into a desired DC voltage and supplies power to each device.

(Structure of Electronic Endoscope 12)

Figure 2:
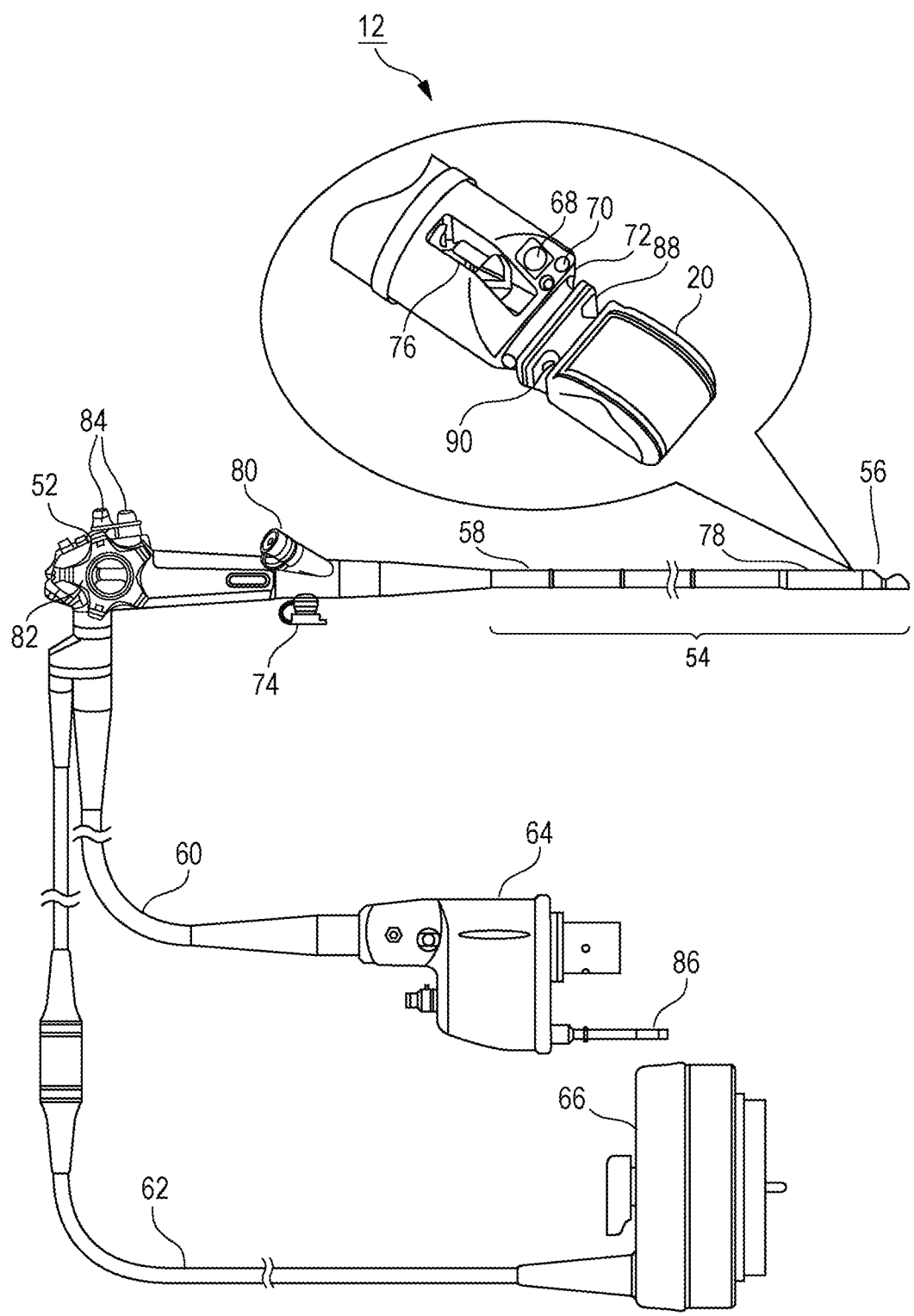
FIG. 2 is a diagram for describing an example of an electronic endoscope that includes an ultrasonic probe used in the electronic endoscope system of the embodiment.

FIG. 2 is a diagram for describing an example of the electronic endoscope that includes the ultrasonic probe used in the electronic endoscope system of the embodiment.

The electronic endoscope 12 includes an operation unit 52, an insertion portion 54 including a distal tip 56 and a soft portion 58 that is mainly provided inside, a flexible cable 60 including a light guide cable inside, a scanner connector cable 62, a connector 64, and a scanner connector 66.

The distal tip 56 is a sensor that examines a biological tissue, and includes an image sensor unit 68, an emission end surface 70, and the ultrasonic probe 20. The ultrasonic probe 20 has a transducer array in which a plurality of ultrasonic transducers, for example, piezoelectric elements is arranged in an array as probe elements. Each of these transducers transmits ultrasonic waves according to a drive signal, receives reflected waves from a subject, and outputs an analog reception signal. Each of the transducers is configured using, for example, an element in which electrodes are formed at both ends of a piezoelectric body including lead zirconate titanate (PZT) which is a piezoelectric ceramic, polyvinylidene difluoride (PVDF) which is a polymer piezoelectric element, or the like.

The image sensor unit 68 of the distal tip 56 is provided with an objective lens and the image sensor 16. The objective lens forms an image of light returning from a biological tissue irradiated with illumination light on a light receiving surface of the image sensor 16. The image sensor 16 is, for example, a single-plate color charge coupled device (CCD) image sensor having a Bayer pixel arrangement. The single-plate color CCD image sensor accumulates the optical image formed by each pixel on the light receiving surface as electrical charge corresponding to a light amount, and generates and outputs image signals corresponding to the color components of red (R), green (G), and blue (B). The image sensor 16 is not limited to the CCD image sensor, and a complementary metal oxide semiconductor (CMOS) image sensor or another type of imaging device can also be used. Further, the image sensor 16 may include a complementary color filter.

Illumination light of the illumination unit 14 passes through a light distribution lens and is emitted from the emission end surface 70 at the distal tip 56. The incident illumination light is emitted from the emission end surface 70 through the light distribution lens. The illumination light is incident on the illumination unit 14 of the electronic endoscope 12 via the light guide 94.

An outer portion of the distal tip 56 includes a hard resin. The image sensor unit 68 is provided with the image sensor 16, and an objective lens, an illumination lens, and the like (not illustrated) for image capturing using the image sensor 16.

The distal tip 56 further includes an air/water supply nozzle 72 that discharges or sucks liquid or gas. The air/water supply nozzle 72 discharges liquid such as water for cleaning surfaces of the objective lens and the illumination lens associated with the image sensor 16, and discharges gas such as air for removing liquid or a foreign matter that remains on the surfaces of the objective lens and the illumination lens. Further, a balloon (not illustrated) used for performing ultrasonic diagnosis by being filled with liquid and bringing the liquid into contact with a biological tissue is attached to the distal tip 56, and a balloon water injection port 88 and a balloon water suction port 90 are provided. Furthermore, the distal tip 56 is provided with a forceps elevator 76 for bringing a flexible puncture needle (not illustrated) into contact with a biological tissue, and is also provided with an opening for sucking liquid or gas on the biological tissue through the forceps elevator 76.

The insertion portion 54 is provided with a bending section 78 that bends in a vertical direction and a horizontal direction. A portion on a proximal end side (the operation unit 52 side) with respect to the bending section 78 is the flexible soft portion 58 that can be bent under its own weight or according to an operation by a practitioner.

The soft portion 58 is provided between the bending section 78 and the operation unit 52, and is provided therein with a signal line of a sensor provided at the distal tip 56 and with a plurality of individual channels through which gas or fluid flows from the above opening. These individual channels are formed by pipes, tubes, or long holes.

On the side of the operation unit 52 and the distal tip 56, a flexible treatment tool insertion port protrusion 80 for inserting a puncture needle and a forceps elevation wire cleaning port 74 are provided in a protruding manner. A cap is detachably attached to an opening of an end portion of the treatment tool insertion port protrusion 80. A flexible treatment tool insertion/suction tube that extends from the treatment tool insertion port protrusion 80 toward the distal tip 56 side is provided inside the insertion portion 54. The treatment tool insertion/suction tube is opened by the forceps elevator 76. The puncture needle inserted into the treatment tool insertion/suction tube from the treatment tool insertion port protrusion 80 can protrude outward from a distal tip opening of the treatment tool insertion/suction tube in the forceps elevator 76, and is used to palpate a biological tissue by protruding from the distal tip opening.

The operation unit 52 includes a plurality of operation buttons 84 of a channel switching switch, and is provided therein with a common channel which extends from the connector 64 and within the flexible cable 60 and through which fluid flows. A bending operation lever 82 is a lever operated by a practitioner to bend the bending section 78 in the vertical direction and the horizontal direction. The bending section 78 is bent in the vertical direction and the horizontal direction according to a rotation operation of the bending operation lever 82.

The flexible cable 60 connects the connector 64, which is connected to the captured image processor 22, and the operation unit 52. The connector 64 is also provided with an opening port of a common channel for supplying or sucking fluid.

The connector 64 includes a light source insertion portion 86 and is connected to the captured image processor 22. Illumination light generated by a light source unit in the captured image processor 22 is transmitted from the connector 64 toward the distal tip 56 through the light guide cable in the flexible cable 60, the operation unit 52, and the insertion portion 54. Furthermore, from the connector 64, a drive signal is sent from the captured image processor 22 to the image sensor 16 via a signal line in the flexible cable 60. An image signal captured by the image sensor 16 is sent to the captured image processor 22 via the signal line in the flexible cable 60, the operation unit 52, and the insertion portion 54.

The scanner connector 66 is connected to the ultrasonic image processor 30, and sends an echo signal scanned by the ultrasonic probe 20 to the ultrasonic image processing unit 32 via the scanner connector cable 62. The ultrasonic image processing unit 32 processes the echo signal to generate a diagnostic image of a biological tissue to be examined, and displays the generated image on the display unit 46. Furthermore, the scanner connector cable 62 transmits the drive signal of the ultrasonic probe 20 from the ultrasonic image processor 30 to the piezoelectric element of the ultrasonic probe 20. The piezoelectric element is capable of converting electrical energy into mechanical energy, and generates ultrasonic waves through expansion and contraction due to voltage changes.

The connector 64 is connected to the driver signal processing unit 18. An image signal of a biological tissue is input from the image sensor 16 to the driver signal processing unit 18 in predetermined frame periods, and is output to a system controller and the captured image processing unit 26 of the captured image processor 22. The frame period is, for example, 1/30 seconds or 1/60 seconds.

(Image Forming Principle of Ultrasonic Image)

Figure 3:
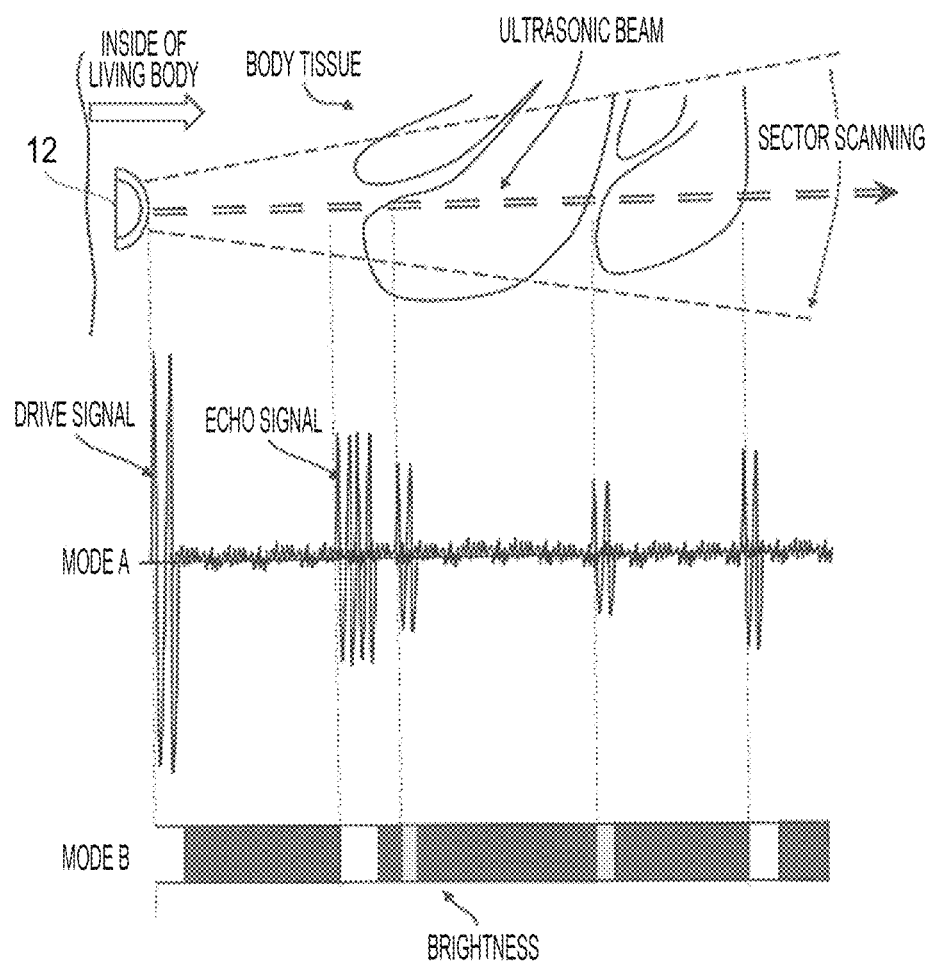
FIG. 3 is a diagram for describing an image forming principle for an ultrasonic image in the electronic endoscope system of the embodiment.

Next, referring to FIG. 3, an image forming principle for an ultrasonic image in the electronic endoscope system of the embodiment is illustrated.

Image formation using ultrasonic waves is based on an ultrasonic pulse reflection method. FIG. 3 illustrates a state where an ultrasonic beam is generated from the ultrasonic probe 20 in a living body. The ultrasonic beam emits, for example, ultrasonic waves of around 10 MHz in the form of a pulse into the living body from the ultrasonic probe 20. The emitted ultrasonic waves become reflected waves due to a difference in acoustic impedance of a body tissue within the living body, and is received again by the ultrasonic probe 20. The reflected waves become an echo signal.

The scanning of the ultrasonic beam by the electronic endoscope 12 is phased array-type sector scanning, and an echo signal along a predetermined direction can be obtained using the sector scanning. FIG. 3 illustrates an example of an echo signal using a mode A display. In the mode A, a horizontal axis represents time, and a vertical axis represents reflection intensity (amplitude), and an echo signal is displayed. The time represents a depth of the living body, and is a distance between body tissues.

As illustrated in FIG. 3, a mode B involves subjecting a waveform of the mode-A echo signal to brightness modification according to the reflection intensity to be converted into brightness, and using the brightness to represent a tomographic image as a grayscale image. An imaging mode of the ultrasonic image processor 30 may further include a well-known mode M and a Doppler mode.

(Signal Processing of Ultrasonic Image Processor 30)

Next, signal processing performed in the ultrasonic image processor 30 of the embodiment will be described in more detail with reference to FIG. 4.

FIG. 4 is a diagram for describing an example of signal processing until an echo signal when an ultrasonic image is acquired is displayed as a mode-B ultrasonic image in the ultrasonic image processor 30 of the embodiment.

As illustrated in FIG. 4, the signal processing unit 36 includes an amplifier circuit 120, an integration circuit 122, an A/D converter 124, a digital filter setting unit 125, and a band limiting filter 126.

An echo signal obtained by the ultrasonic probe 20 is amplified by the amplifier circuit 120 and integrated by the integration circuit 122 to remove harmonic noise. The amplifier circuit 120 and the integration circuit 122 may include an amplification function and a low-pass filter function due to an integrated inverting amplification-type integration circuit. Next, the echo signal, which is an analog signal, is digitized (binarized) by the A/D converter 124 in a sampling period using a clock signal, thus becoming a digital echo signal.

In the embodiment, the band limiting filter 126 (an example of a filter processing unit) performs band limitation on the digital echo signal on the basis of a digital filter setting value set by the digital filter setting unit 125. The band limiting filter 126 is, for example, a low-pass filter or a band-pass filter. A cutoff frequency in a case where the band limiting filter 126 is a low-pass filter or a cutoff frequency on a high frequency side in a case where the band limiting filter 126 is a band-pass filter is lower than a cutoff frequency by the integration circuit 122.

As illustrated in FIG. 4, the ultrasonic image processing unit 32 includes a brightness modification unit 128, an ultrasonic image generation unit 130, and a D/A converter 132.

The digital echo signal output from the signal processing unit 36 is subjected to brightness modification according to reflection intensity by the brightness modification unit 128 and converted into brightness. The digital echo signal thus converted into brightness is subjected to image processing in the ultrasonic image generation unit 130 and becomes a two-dimensional mode-B tomographic image. This digital image signal is converted into an analog signal by the D/A converter 132, and is displayed as a mode-B tomographic image by the display unit 46.

The noise frequency detection unit 34 (an example of the frequency band detection unit) detects a frequency band of a noise component included in the echo signal and equal to or higher than a preset threshold level.

That is, since a frequency component of an echo signal not including noise (ultrasonic reception signal) is known, the frequency band of the noise component equal to or higher than the preset threshold level is specified from bands excluding the frequency component of the ultrasonic signal by performing frequency analysis using fast Fourier transform (FFT). It is preferable to increase a sampling rate of the A/D converter 124 in order to grasp broadband frequency characteristics including a frequency band including less noise.

The digital filter setting unit 125 of the signal processing unit 36 performs filter setting (that is, filter setting in the band limiting filter 126) on the echo signal so that a signal in the frequency band detected by the noise frequency detection unit 34 is attenuated.

(Content of Filter Processing)

Next, content of filter processing performed by the digital filter setting unit 125 and the band limiting filter 126 in the signal processing unit 36 will be described with reference to FIGS. 5A to 8.

The band limiting filter 126 of the embodiment is a low-pass filter that attenuates a signal of a frequency component equal to or higher than a predetermined frequency including a frequency band of a noise component detected by the noise frequency detection unit 34 in an echo signal. FIG. 5A illustrates a spectrum of an ultrasonic signal included in the echo signal and a filter characteristic of the low-pass filter defined by the integration circuit 122 of the signal processing unit 36. Here, in a case where the frequency band of the noise detected by the noise frequency detection unit 34 is a frequency band higher than the ultrasonic signal as illustrated in a spectrum of the echo signal of FIG. 5B, a low-pass filter (filter characteristic of FIG. 5B) is set such that the detected noise of the frequency band is attenuated. In the filter characteristic of FIG. 5B, the cutoff frequency is set to be lower than that in the filter characteristic (by the integration circuit 122) of FIG. 5A, so that noise is effectively removed.

As illustrated in FIG. 5C, in a case where both a lower band and a higher band than the frequency band of the ultrasonic signal exist in the frequency band of the noise component detected by the noise frequency detection unit 34, it is preferable to set a band-pass filter as the band limiting filter 126.

The band limiting filter 126 of the embodiment has filter characteristics suitable for tissue harmonic imaging (THI) in a case where the ultrasonic image processing unit 32 generates an image corresponding to the THI. The THI is known as an imaging method for generating an ultrasonic image on the basis of equal to or greater than two harmonic components having a frequency of N times (N: an integer of equal to or greater than 2) a fundamental frequency, which are generated by distortion of an ultrasonic waveform accompanying propagation, and generally has an effect of improving resolution and reducing artifacts.

Figure 6:
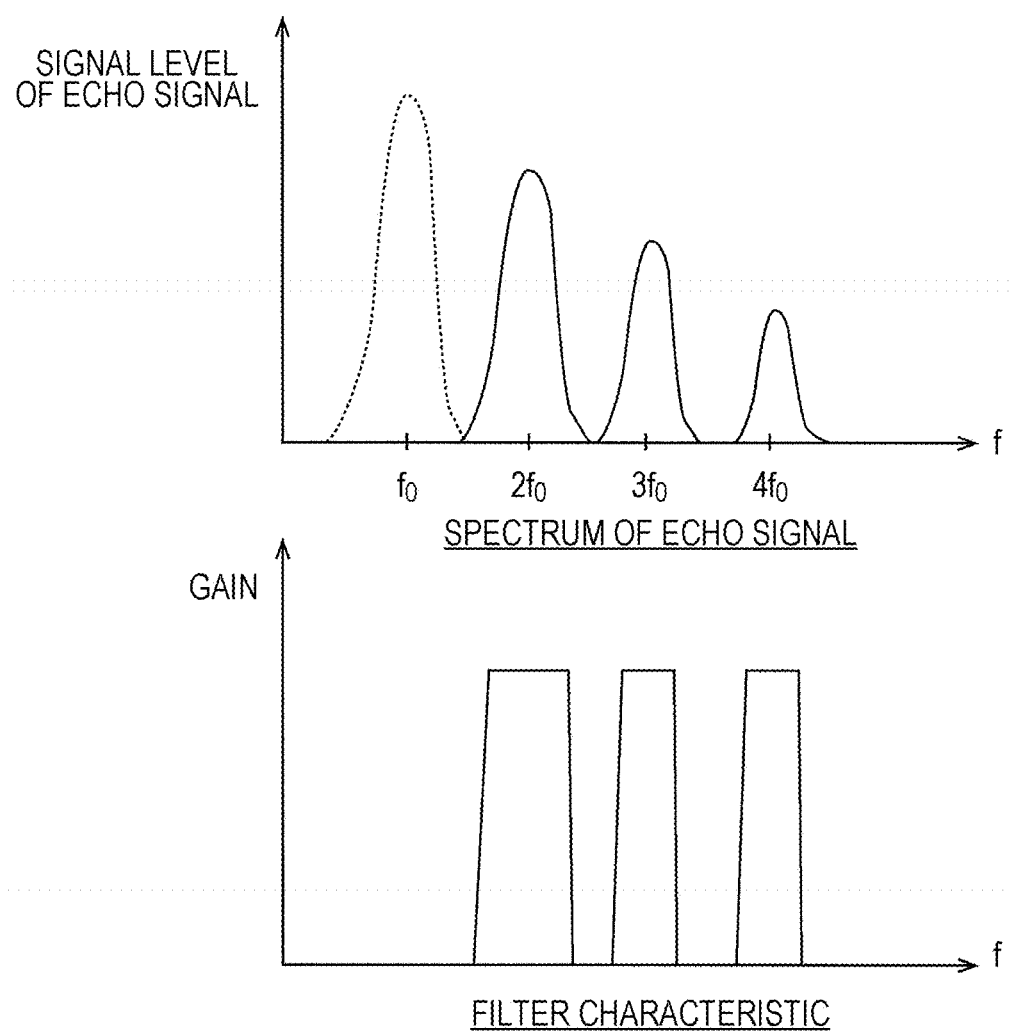
FIG. 6 is a diagram for describing an example of the filter characteristic applied to the echo signal.

Referring to FIG. 6, the spectrum of the echo signal includes a signal component having a fundamental frequency $f_0$ as a center frequency, and harmonic components of a secondary component, a tertiary component, a quaternary component, . . . having frequencies $2f_0$, $3f_0$, $4f_0$, . . . of N times (N: an integer of equal to or greater than 2) the fundamental frequency as the center frequencies. In this case, since the frequencies $2f_0$, $3f_0$, $4f_0$, . . . are known, the noise frequency detection unit 34 specifies (detects) a frequency band of a noise component equal to or higher than a preset threshold level from bands excluding frequency bands having the frequencies $2f_0$, $3f_0$, $4f_0$, . . . as the center frequencies. Then, the digital filter setting unit 125 performs filter setting on the echo signal so that a signal in the frequency band detected by the noise frequency detection unit 34 is attenuated (that is, so that signals of frequencies other than N times the fundamental frequency are attenuated). As a result, the filter characteristic of the band limiting filter 126 can be, for example, a characteristic of a band-pass filter as illustrated in FIG. 6.

In the embodiment, it is also effective to increase pulse duration of an ultrasonic pulse transmitted from the ultrasonic probe to a biological tissue. Since a bandwidth of an ultrasonic signal included in an echo signal is narrowed by increasing the pulse duration of the ultrasonic pulse, the filter characteristic can be set so that noise can be effectively removed.

Thus, the control unit 40 (see FIG. 4) may function as an adjustment unit that controls the transmission/reception unit 38 so as to adjust the pulse duration of the ultrasonic pulse applied to the biological tissue by the ultrasonic probe. In that case, the digital filter setting unit 125 performs filter setting on the band limiting filter 126 on the basis of the pulse duration adjusted by the control unit 40.

Referring to FIG. 7, an ultrasonic pulse before a change (pulse duration Tp1) and an ultrasonic pulse after the change (pulse duration Tp2; where Tp2>Tp1) are illustrated. In this case, as illustrated as a spectrum of an echo signal in FIG. 7, an ultrasonic signal received by the ultrasonic pulse after the change has a narrower band than that before the change (indicated by a chain line). Therefore, for example, as illustrated in FIG. 7, even in a case where the frequency bands of the ultrasonic signal received by the ultrasonic pulse before the change and noise overlap with each other, the frequency bands of the ultrasonic signal and the noise can be distinguished after the change of the ultrasonic pulse. Thus, as illustrated in FIG. 7, by setting a band-pass filter such that a signal in a frequency band of detected noise is attenuated as the filter characteristic of the band limiting filter 126, only a noise component can be effectively attenuated.

In a case where a frequency band of a relatively large noise component detected by the noise frequency detection unit 34 and a frequency band of an ultrasonic signal overlap or are close to each other, it is possible to effectively attenuate a noise level without attenuating a signal level of the ultrasonic signal by shifting the frequency band of the ultrasonic signal.

Thus, in the embodiment, the control unit 40 of the ultrasonic image processor 30 functions as a frequency changing unit that changes a frequency of an ultrasonic wave applied to a biological tissue by the ultrasonic probe so as not to overlap with a frequency band of a noise component detected by the noise frequency detection unit 34.

Figure 8:
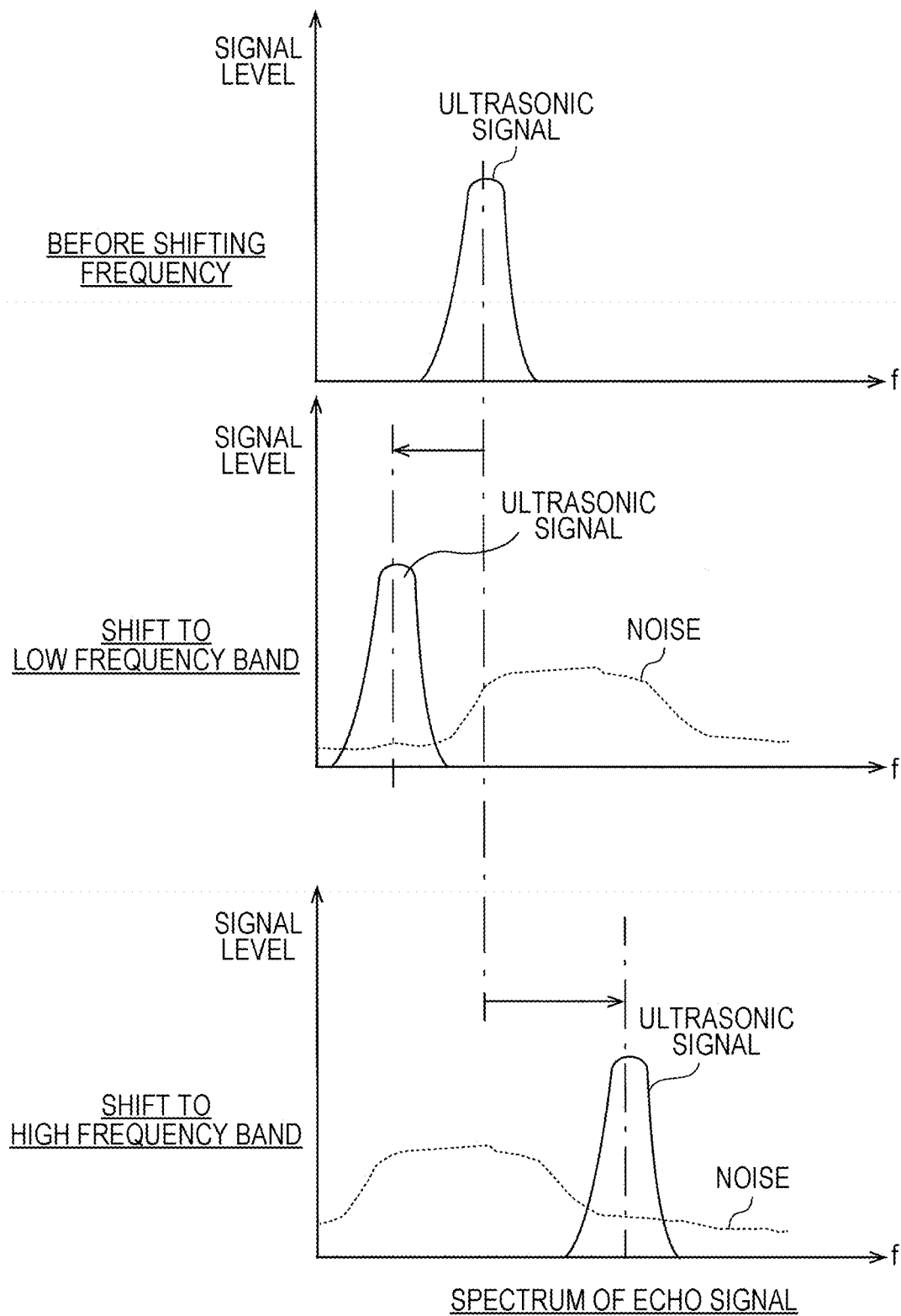
FIG. 8 is a diagram for describing an example of the filter characteristic applied to the echo signal.

For example, in a case where a spectrum (before shifting a frequency) of an ultrasonic signal illustrated in FIG. 8 is assumed, in a case where the frequency band of the ultrasonic signal overlaps with the frequency band of the noise component detected by the noise frequency detection unit 34, the frequency band of the ultrasonic signal is shifted in a low direction (shifted to a low frequency band in FIG. 8) or shifted in a high direction (shifted to a high frequency band in FIG. 8) according to the frequency band of the noise component. Also in this case, the filter characteristic of the band limiting filter 126 can be set so that noise in the detected frequency band is effectively attenuated.

As described above, since the digital filter setting unit 125 and the band limiting filter 126 perform the filter processing on a received echo signal in consideration of a frequency band of a noise component detected by the noise frequency detection unit 34, it is possible to effectively suppress unintended noise.

In a case where the noise is not removed by any of the content of the filter processing described above or a combination thereof, it is conceivable to adopt, in consideration of a fact that the noise is often generated at regular intervals (that is, periodically), a method of removing the periodically generated noise. Such periodic noise includes, for example, a noise component generated by synchronization of a frequency of a clock signal used in a plurality of constituent devices or a frequency which is an integral multiple of a frequency of a switching signal of a plurality of constituent devices, a noise component generated in the switching power supply, and a noise component generated in the insertion portion 54 of the electronic endoscope 12. Suppression of the periodically generated noise component includes a method of suppressing a periodic noise component included in an echo signal, and a method of eliminating a noise pixel by performing image processing on a two-dimensional mode-B image obtained from an echo signal including a noise component.

(Suppression of Amplification Gain of Noise Component)

As described above, as the method of suppressing a periodic noise component included in an echo signal, in the embodiment, the ultrasonic image processing unit 32 may perform gain change processing so that an amplification gain value is changed between a noise pixel and a pixel other than the noise pixel in an ultrasonic image corresponding to the noise component.

In this case, the ultrasonic image processing unit 32 sets a threshold of a noise level in advance, and determines, as the noise component, a signal equal to or greater than the set threshold among digital echo signals (echo signals before being subjected to the processing of the brightness modification unit 128) obtained from the band limiting filter 126. A period (for example, T1, T2, T3, . . . ) of the digital echo signal detected as the noise component is measured. The period (T1, T2, T3, . . . ) can be obtained by, for example, specifying, from a waveform of the digital echo signal of a mode-A display, a plurality of noise component generation time points by using a period calculated from a peak frequency of a power spectrum obtained through frequency analysis using FFT of the digital echo signal, and by calculating a time interval between the generation time points.

The measured period (T1, T2, T3, . . . ) varies within a certain range, and the ultrasonic image processing unit 32 obtains the range of the variation, a maximum value Tmax of the period, and a maximum value Tmin of the period. The digital filter setting unit 125 uses a period width detected by the ultrasonic image processing unit 32 as a bandwidth in a frequency domain, and designs the band limiting filter 126 that removes a frequency band with a minimum frequency 1/Tmax and a maximum frequency 1/Tmin (sets a removal band). As a digital echo signal passes through the band limiting filter 126, even in a case where a noise component is periodically generated in an echo signal, an amplitude of the noise component can be suppressed, and a periodic noise component in a mode-B image can be suppressed.

Figure 9:
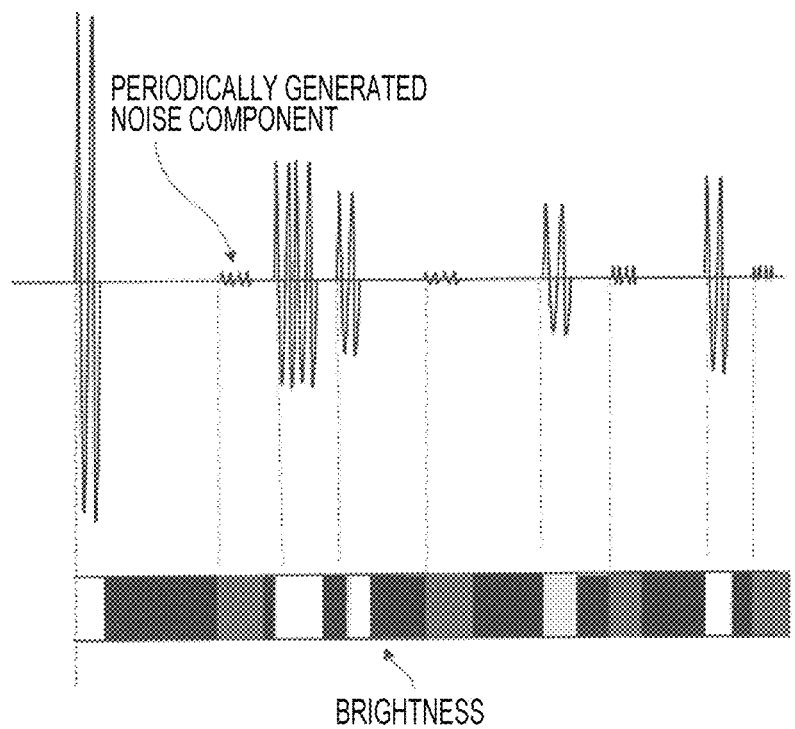
FIG. 9 is a diagram illustrating an example of a digital echo signal after an echo signal including periodically generated noise obtained by the electronic endoscope system of the embodiment passes through a band limiting filter and a brightness.

FIG. 9 is a diagram illustrating an example of a digital echo signal after an echo signal including periodically generated noise obtained by the electronic endoscope system of the embodiment passes through a band removal filter. Harmonic noise is suppressed by the integration circuit 122, and a digital echo signal after passing through the band limiting filter 126 is also suppressed. As a result, a periodically generated noise component in a brightness signal obtained by the brightness modification unit 128 is suppressed.

(Interpolation Processing of Noise Pixel Value)

Figure 10:
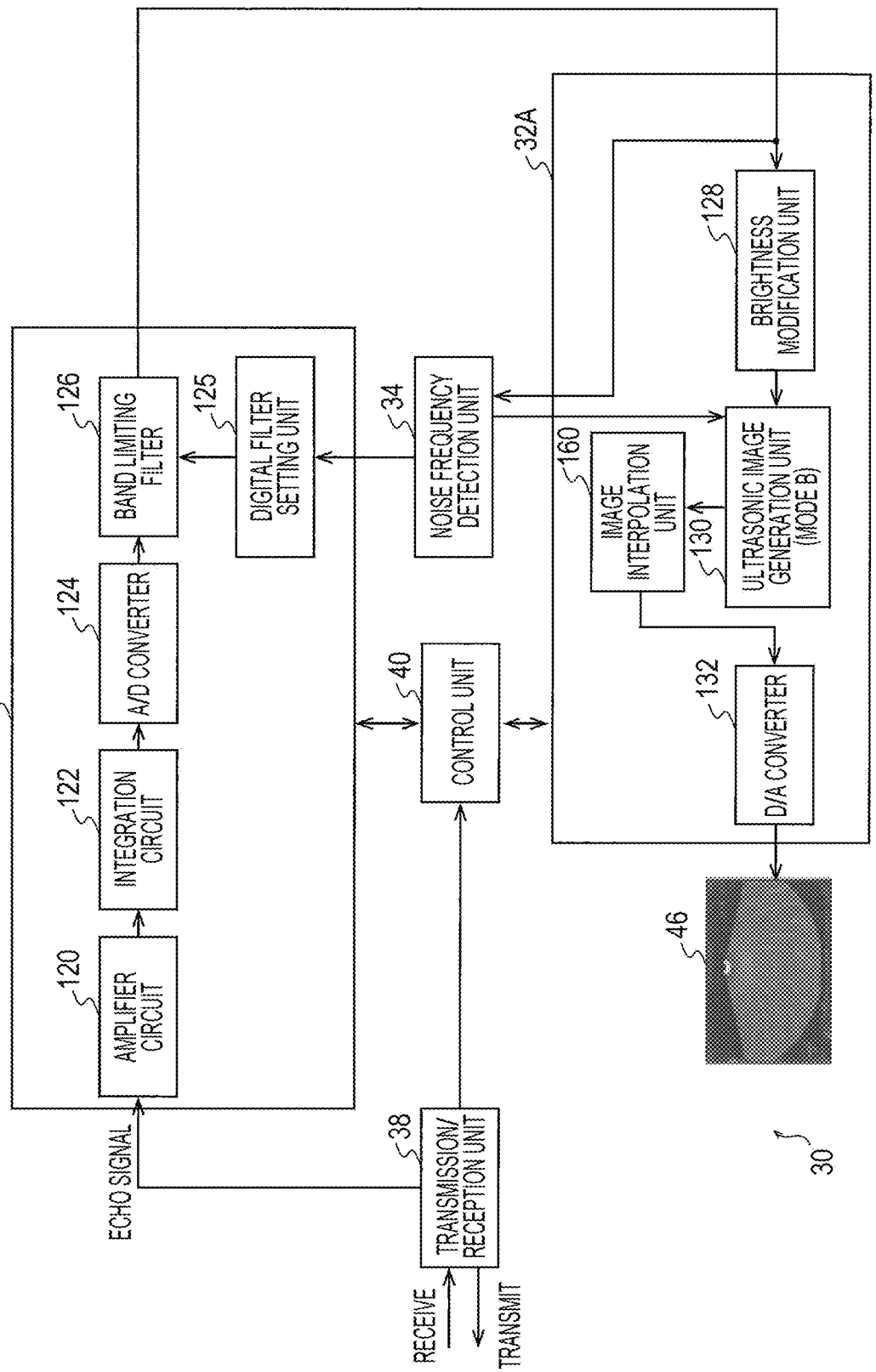
FIG. 10 is a diagram for describing an example of the signal processing until an echo signal when an ultrasonic image is acquired is displayed as a mode-B ultrasonic image in the electronic endoscope system of the embodiment.

As described above, as the method of suppressing a periodic noise component included in an echo signal, in the embodiment, a method of eliminating a noise pixel by performing image processing on a two-dimensional mode-B image obtained from an echo signal including a noise component can be adopted. FIG. 10 illustrates a configuration of the ultrasonic image processor 30 in this case. FIG. 10 differs from FIG. 4 in an ultrasonic image processing unit 32A. The ultrasonic image processing unit 32A is obtained by adding an image interpolation unit 160 to the ultrasonic image processing unit 32. The image interpolation unit 160 replaces a pixel value at a noise pixel position in an ultrasonic image corresponding to a noise component with an interpolation pixel value generated on the basis of pixel values of peripheral pixels positioned around the noise pixel position.

For example, the image interpolation unit 160 performs pixel interpolation by using four peripheral pixels adjacent to four sides of a noise pixel. A pixel value of the noise pixel is pixel-interpolated using pixel values of the four adjacent peripheral pixels. For example, an average value of the pixel values of the four peripheral pixels is set as the pixel value of the noise pixel. This interpolation method is a method called bilinear interpolation, but the interpolation method may be another method. For example, bicubic interpolation is used. In a case where noise pixels are adjacent to each other, the image interpolation unit 160 searches for a pixel adjacent to the noise pixels until a non-noise pixel adjacent to the noise pixels is found, and performs pixel interpolation by using pixel values of a plurality of non-noise pixels surrounding a region of the noise pixels.

In this way, since the signal processing unit 36 performs correction processing of replacing a pixel value of a detected noise component at a noise pixel position in an ultrasonic image with an interpolation pixel value generated on the basis of pixel values of peripheral pixels positioned around the noise pixel position, it is possible to suppress a noise component in a mode-B image even when the noise component is periodically generated in an echo signal.

(Flow of Noise Suppression)

Figure 11:
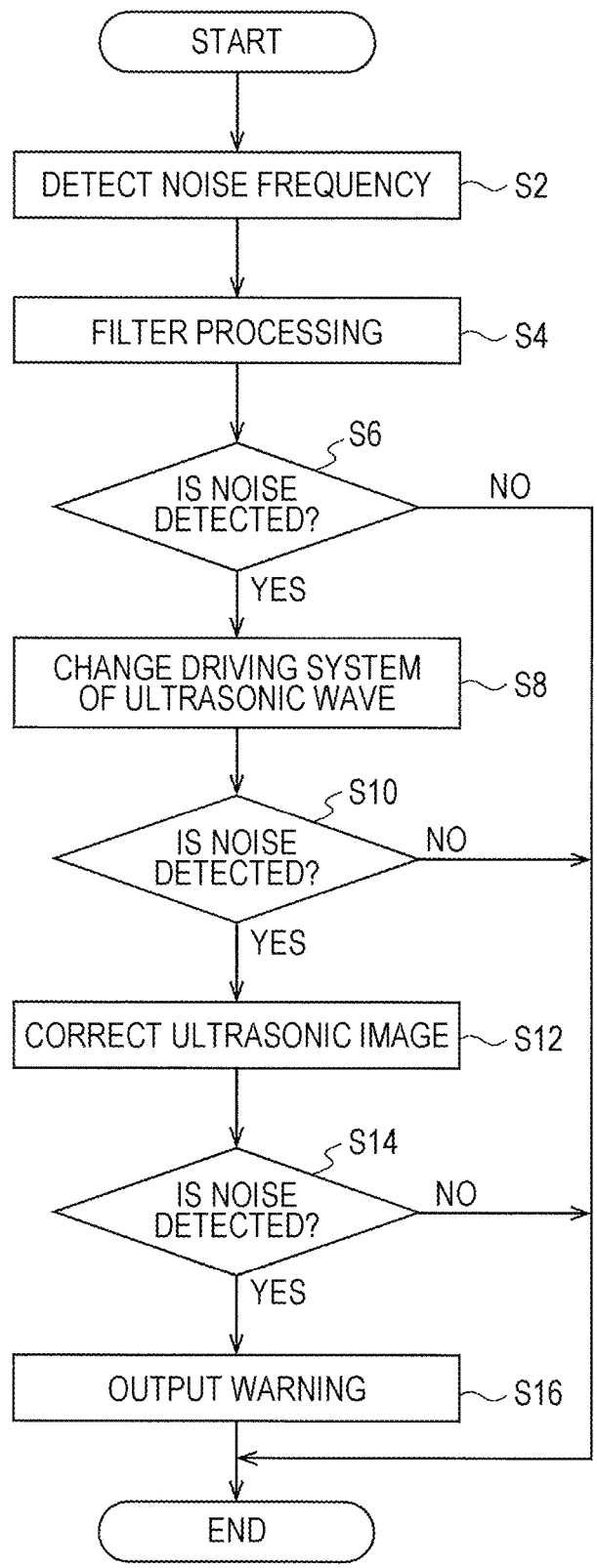
FIG. 11 is a diagram illustrating an example of an operation flow of noise correction performed in the electronic endoscope system of the embodiment.

FIG. 11 is a diagram illustrating an exemplary operation flow of noise correction.

First, in step S2, a frequency band of noise included in a received echo signal is detected. For example, a frequency band of a noise component included in the echo signal and equal to or higher than a preset threshold level is detected. Next, in step S4, filter processing is performed on the echo signal so that a signal in the detected frequency band is attenuated. As a result of the filter processing, in a case where noise equal to or higher than the preset threshold level is not detected (step S6: NO), the processing ends.

In a case where the noise is detected in step S6, it means that the filter processing in step S4 is not sufficient for noise suppression. Thus, a driving system of an ultrasonic wave is changed (step S8), pulse duration of an ultrasonic pulse is lengthened, a bandwidth of an ultrasonic signal included in the echo signal is narrowed, and filter setting corresponding to the narrowband ultrasonic signal is performed. Further, in step S8, a frequency band of the ultrasonic signal may be shifted to perform filter setting corresponding to the shifted frequency band. Then, it is determined again whether or not noise equal to or higher than the preset threshold level is detected, and in a case where the noise is not detected (step S10: NO), the processing ends.

In a case where the noise is detected in step S10, it means that the change of the driving system of the ultrasonic wave in step S8 is not effective. Thus, in step S12, a two-dimensional mode-B image obtained from the echo signal including the noise component is corrected. In the image correction, a pixel value at a noise pixel position in an ultrasonic image corresponding to the noise component is replaced with an interpolation pixel value generated on the basis of pixel values of peripheral pixels positioned around the noise pixel position. Then, it is determined again whether or not noise equal to or higher than the preset threshold level is detected, and in a case where the noise is not detected (step S14: NO), the processing ends.

In a case where the noise is detected in step S14, a warning is output in Step S16, and the processing ends. The warning is output by being displayed on the display unit 46. In this case, a practitioner is notified of presence of the noise so as not to affect diagnosis using the ultrasonic image.

The electronic endoscope system of the present invention has been described above in detail, but the electronic endoscope system of the present invention is not limited to the above embodiment. As a matter of course, various improvements or modifications may be made within a scope not departing from the concept of the present invention.

The present invention relates to a patent application of Japanese Patent Application No. 2021-169093 filed with the Japan Patent Office on Oct. 14, 2021, the entire contents of which are incorporated herein by reference.

The invention claimed is:

1. An electronic endoscope system that acquires an ultrasonic image, the electronic endoscope system comprising:
an electronic endoscope including, at a distal tip, an image sensor that captures an image of a biological tissue, and an ultrasonic probe that applies ultrasonic waves to the biological tissue to obtain an echo signal;
   a captured image processor including an image processing unit that processes an imaging signal output from the image sensor and generates a captured image; and
   an ultrasonic image processor that processes the echo signal output from the ultrasonic probe and generates an ultrasonic image, and detects a frequency band of a noise component included in the echo signal and that is equal to or higher than a preset threshold level, and wherein the ultrasonic image processor includes a filter that performs filter processing on the echo signal by attenuating a signal in the detected frequency band of the noise component based on a filter characteristic set by the ultrasonic image processor and wherein:
   the ultrasonic image processor adjusts a pulse duration of an ultrasonic wave applied to the biological tissue by the ultrasonic probe resulting in a narrower frequency band of the echo signal and the ultrasonic image processor adjusts the filter characteristic of the filter to attenuate the noise component outside the narrower frequency band of the echo signal, and
   the filter performs filter processing on the echo signal based on the adjusted pulse duration.

2. The electronic endoscope system according to claim 1, wherein
   the ultrasonic image processor includes a low-pass filter that attenuates a signal of a frequency component that is equal to or higher than a predetermined frequency in the echo signal, and
   the filter processing unit performs the filter processing, wherein a signal of a frequency component that is lower than the predetermined frequency in the echo signal is attenuated.

3. The electronic endoscope system according to claim 1, wherein
   the echo signal includes a signal component of a fundamental frequency and equal to or greater than two harmonic components having a frequency N times the fundamental frequency,
wherein N is an integer of equal to or greater than 2,
   the ultrasonic image processor generates the ultrasonic image on the basis of the equal to or greater than two harmonic components, and
   the filter performs the filter processing on the echo signal, wherein a signal having a frequency other than the frequency N times the fundamental frequency is attenuated.

4. The electronic endoscope system according to claim 1, wherein
   the ultrasonic image processor includes a frequency changing unit that changes a frequency of an ultrasonic wave applied to the biological tissue by the ultrasonic probe to not to overlap with the frequency band of the noise component detected by the frequency band detection unit.

5. The electronic endoscope system according to claim 1, wherein
   the ultrasonic image processing unit performs gain change processing to change an amplification gain value between a noise pixel that is a position in the ultrasonic image corresponding to the noise component included in the echo signal and a pixel other than the noise pixel in the ultrasonic image.

6. The electronic endoscope system according to claim 1, wherein
   the ultrasonic image processing unit replaces a pixel value at a noise pixel that is a position in the ultrasonic image corresponding to the noise component included in the echo signal with an interpolation pixel value generated on the basis of pixel values of peripheral pixels positioned around the noise pixel position.

* * * * *